United States Patent
Yamashita et al.

(12)

(10) Patent No.: US 6,210,900 B1
(45) Date of Patent: *Apr. 3, 2001

(54) METHOD OF ENCODING A SERIES OF COMBINATORIAL LIBRARIES AND DEVELOPING STRUCTURE ACTIVITY RELATIONSHIPS

(75) Inventors: Dennis Shinji Yamashita, King of Prussia; Joseph Weinstock, Phoenixville, both of PA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/537,752
(22) PCT Filed: May 23, 1995
(86) PCT No.: PCT/US95/06392
    § 371 Date: Nov. 22, 1996
    § 102(e) Date: Nov. 22, 1996
(87) PCT Pub. No.: WO95/32425
    PCT Pub. Date: Nov. 30, 1995
(51) Int. Cl.$^7$ .............................. C12Q 1/00; G01N 33/53; G01N 33/566; G01N 33/543
(52) U.S. Cl. ............................ 435/7.1; 435/4; 436/501; 436/518; 436/524; 436/528; 436/529; 436/530; 436/531; 436/164; 436/182

(58) Field of Search ..................... 435/7.1, 4, DIG. 46, 435/DIG. 21; 436/501, 518, 524, 528, 529, 530, 531, 164, 182

(56) References Cited

U.S. PATENT DOCUMENTS 5,639,603 * 6/1997 Dowe et al. ............................ 435/6

FOREIGN PATENT DOCUMENTS

93/24517 * 12/1993 (WO).

OTHER PUBLICATIONS

Proceedings of the National Academy of Sciences USA, vol. 90, Issued Nov. 1993, Needels et al., pp. 10700–10704.
Nature, vol. 354, Issued Nov. 7, 1991, Lam et al., pp. 82–84.
Proceedings of the National Academy of Sciences USA, vol. 90, Issued Dec. 1993, Ohlmeyer et al., pp. 10922–10926.
K.C. Nocolaou, et al., Chem. Ed. Engl.; 1995, vol. 34, No. 20, pp. 2289–2291.

* cited by examiner

*Primary Examiner*—Jyothsna Venkat
*Assistant Examiner*—Joseph W. Ricigliano
(74) *Attorney, Agent, or Firm*—Wayne J. Dustman; William T. King; Charles M. Kinzig

(57) ABSTRACT

Invented is a method of preparing combinatorial libraries and combinatorial libraries prepared thereby. Also invented is a method for identifying compounds having desired characteristics from a combinatorial library or a set of combinatorial libraries by the use of flow cytometry. Also invented is a method for encoding combinatorial libraries using fluorophore labeled beads.

4 Claims, No Drawings

METHOD OF ENCODING A SERIES OF COMBINATORIAL LIBRARIES AND DEVELOPING STRUCTURE ACTIVITY RELATIONSHIPS

FIELD OF THE INVENTION

The field of this invention concerns combinatorial chemistry which involves the syntheses of one or more encoded combinatorial libraries where large numbers of products having varying compositions are obtained. This invention also relates to methods of encoding combinatorial libraries.

BACKGROUND OF THE INVENTION

In the continuing search for new chemical moieties that can effectively modulate a variety of biological processes, the standard method for conducting a search is to screen a variety of pre-existing chemical moieties, for example, naturally occurring compounds or compounds which exist in synthetic libraries or databanks. The biological activity of the pre-existing chemical moieties is determined by applying the moieties to an assay which has been designed to test a particular property of the chemical moiety being screened, for example, a receptor binding assay which tests the ability of the moiety to bind to a particular receptor site.

In an effort to reduce the time and expense involved in screening a large number of randomly chosen compounds for biological activity, several developments have been made to provide libraries of compounds for the discovery of lead compounds. The chemical generation of molecular diversity has become a major tool in the search for novel lead structures. Currently, the known methods for chemically generating large numbers of molecularly diverse compounds generally involve the use of solid phase synthesis, in particular to synthesize and identify peptides and peptide libraries. See, for example, Lebl et al., *Int. J. Pept. Prot. Res.*, 41, p. 201 (1993) which discloses methodologies providing selectively cleavable linkers between peptide and resin such that a certain amount of peptide can be liberated from the resin and assayed in soluble form while some of the peptide still remains attached to the resin, where it can be sequenced; Lam et al., *Nature*, 354, p. 82 (1991) and (WO 92/00091) which disclose a method of synthesis of linear peptides on a solid support such as polystyrene or polyacrylamide resin; Geysen et al., *J. Immunol. Meth.*, 102, p. 259 (1987) which discloses the synthesis of peptides on derivatized polystyrene pins which are arranged on a block in such a way that they correspond to the arrangement of wells in a 96-well microtiter plate; and Houghten et al., *Nature*, 354, p. 84 (1991) and WO 92/09300 which disclose an approach to de novo determination of antibody or receptor binding sequences involving soluble peptide pools.

The major drawback, aside from technical considerations, with all of these methods for lead generation is the quality of the lead. Linear peptides historically have represented relatively poor leads for pharmaceutical design. In particular, there is no rational strategy for conversion of a linear peptide into a non-peptide lead. As noted above, one must resort to screening large databanks of compounds, with each compound being tested individually, in order to determine non-peptide leads for peptide receptors.

It is known that a wide variety of organic reactions can be carried out on substrates immobilized on resins. These include, in addition to peptide synthesis reactions which are well known to those of ordinary skill in the art, nucleophilic displacements on benzylic halides, halogenation, nitration, sulfonation, oxidation, hydrolysis, acid chloride formation, Friedel-Crafts reactions, reduction with $LiAlH_4$, metallation, and reaction of the organometallic polymer with a wide variety of reagents. See, for example, N. K. Mathur et al., *Polymers as Aids in Organic Chemistry*, Academic Press, New York, p. 18 (1980). In addition, Farrall et al., *J. Org. Chem.*, 41, p. 3877 (1976) describe the experimental details of some of these reactions carried out with resins.

Nonpeptidic organic compounds, such as peptide mimetics, can often surpass peptide ligands in affinity for a certain receptor of enzyme. An effective strategy for rapidly identifying high affinity biological ligands, and ultimately new and important drugs, requires rapid construction and screening of diverse libraries of non-peptidic structures containing a variety of structural units capable of establishing one or more types of interactions with a biological acceptor (e.g., a receptor or enzyme), such as hydrogen bonds, salt bridges, pi-complexation, hydrophobic effects, etc. However, work on the generation and screening of synthetic test compound libraries containing nonpeptidic molecules is now in its infancy. one example from this area is the work of Ellman and Bunin on a combinatorial synthesis of benzodiazepines on a solid support (J. Am. Chem. Soc. 114, 10997, (1992); see *Chemical and Engineering News,* Jan. 18, 1993, page 33).

A key unsolved problem in the area of generation and use of nonpeptide libraries is the generation and use of nonpeptide libraries is the elucidation of the structure of molecules selected from a library that show promising biological activity.

An attempt to uncover the structures of peptides selected from a library using unique nucleotide sequence codes. which are synthesized in tandem with the peptide library, has been described by Brenner and Lerner (Brenner, S. and Lerner, R. A. *Proc. Nat'l. Acad. Sci. USA,* 1992 89. 5381–5383). The nucleotide sequence of the code attached to each peptide must be amplifiable via the polymerase chain reaction (PCR). However, nucleotide synthesis techniques are not compatible with all of the synthetic techniques required for synthesis of many types of molecular libraries. Furthermore, the close proximity of nucleotide and synthetic test compound in the library, which can result in interactions between these molecules interfering with the binding of the ligand with a target receptor of enzyme during the biological assay, also limits this approach. The nucleotide component of the library can also interfere during biological assays in a variety of other ways.

Kerr et al. (*J. Am. Chem. Soc.,* 1993, 115, 2520–2531) reported synthesizing solution phase libraries of peptides, containing non-natural amino acid residues, in parallel with peptide coding strands. The peptide ligand and its coding strand in this library are covalently joined together, which allows isolation and sequence determination of pairs of synthetic test compound and corresponding code. However, as with the nucleic-acid-encoded library described by Brenner and Lerner, above, the coding peptide may interfere with the screening assay.

PCT/US93/09345 describes a method of identifying actives in a combinatorial library by attaching multiple tags in a predetermined binary coding system.

PCT/HU93/0030 describes fluorescently labeled sublibrary peptide kits for use in peptide synthesis.

PCT/US94/06078 describes methods of encoding combinatorial libraries using polymeric sequences.

Many of the disadvantages of the known methods as well as many of the needs not met by them are addressed by the present invention which, as described more fully hereinafter, provides numerous advantages over the known methods.

SUMMARY OF THE INVENTION

This invention relates to a method for identifying compounds having desired characteristics and identifying essential moieties in a lead structure which comprises preparing one or more encoded combinatorial libraries from a specified set of reaction sequences and testing compounds therein for biological activity.

This invention also relates to a method of encoding a single registry in each combinatorial library of a series of combinatorial libraries and combinatorial libraries with a single encoded registry.

This invention also relates to a method of encoding combinatorial libraries which comprises utilization of tagged beads.

This invention also relates to a method of encoding each choice of a combinatorial library and combinatorial libraries encoded thereby.

This invention also relates to beads with fluorescently labeled identifiers attached thereto.

DETAILED DESCRIPTION OF THE INVENTION

As used herein, the term "beads" means any solid support material capable of providing a base for combinatorial syntheses and capable of being processed by flow cytometry, such as 1 to 2% crosslinked polystyrene, polyacrylamide, polyethylene glycol polystyrene co-polymer, preferably Tentagel 10 to 100 micron particles, most preferably Tentagel 10–30 micron particles.

As used herein, the term "sort" means to form beads into groups which have a common tagging aspect by flow cytometry.

As used herein, the term "separate" or "split" when referring to encoded beads or beads of a combinatorial library means to partition the mixture of beads into groups, each group thereinby containing a mixture, preferably a statistical mean of all members.

As used herein, the term "tag", unless otherwise indicated, means an encoding characteristic of a bead or group of beads which is capable of being sorted by flow cytometry, such as differences in size, differences in material composition, differences in flow properties, a single fluorescent marker or, preferably, a fluorescent label identifier.

As used herein, the term "fluorescent label identifier" or "identifier" means a coding label attached to a bead or group of beads either by adding ratios of a fluorophore and a non-fluorophore or by adding multiple, preferably two, different fluorophores in varying ratios.

As used herein, the term "intensity-differentiated" means an identifier (as used herein) in which varying ratios of a fluorophore and a non-fluorophore are added to a bead or group of beads.

As used herein, the term "choice" means the alternative variables for a given stage in a combinatorial synthesis (not limited to peptide chemistry), such as reactant, reagent, reaction conditions, and combinations thereof. Where the term "stage" corresponds to a step in the sequential synthesis of a compound or ligand; the compound or ligand being the final product of a combinatorial synthesis. The term "registry", as used herein, has the same meaning as the term "stage" as indicated above.

In a preferred aspect of the invention a series of combinatorial libraries are prepared, each individual library being prepared from substantially the same specified set of reaction sequences, therein encoding a single registry within each combinatorial library and analyzing according to mixtures of compounds with a homogeneous registry. Preferably, the specific encoded registry of any library will be different from the other libraries and the number of libraries prepared will equal the number of registries in a single library.

In carrying out the synthesis to prepare the first library, one may initially begin with a number of beads, usually at least $10^3$, more usually at least $10^4$, and desirably at least $10^5$, while generally not exceeding at least $10^{15}$, more usually not exceeding at least $10^{10}$, characterized in that the beads are separated into groups, the beads within each group being similarly tagged and each group being uniquely tagged, preferably by an identifier, or one group being untagged and each of the remaining groups being uniquely tagged, preferably by an identifier. The number of readily identifiable groups of beads will correspond to the number of choices in the first registry, the entirety of each group is entered into a separate container. One can use microtiter well plates, flasks, Merrifield synthesis vessels, etc. The beads will usually be divided up into groups of at least one bead each, usually a plurality of beads, generally 1000 or more, and may be $10^5$ or more depending on the total number of registries involved in the library.

One would then add the appropriate agents to each of the individual containers to process them in stages (or "registries" as used herein). Once the reaction(s) is complete, one may wish to wash the beads free of any reagent, followed by combining all of the beads into a single mixture and then separating the beads according to the number of choices for the next registry. The procedure of dividing beads, followed by a synthetic stage (to form a registry), and then recombining beads is iterated until the first combinatorial library is completed.

In some instances, the same reaction may be carried out in 2 or more containers to enhance the proportion of product having a particular reaction in a particular registry as compared to the other choices. In other instances, one or more of the registries may involve a portion of the beads being set aside and undergoing no reaction, so as to enhance the variability associated with the final product. In other situations, batches may be taken along different synthetic pathways.

The library thus prepared will contain tagged beads which identify the reaction sequence of the first registry only.

A combinatorial library containing tagged beads which identify the reaction sequence of the first registry only can be prepared as outlined in Scheme 1 below.

Scheme 1
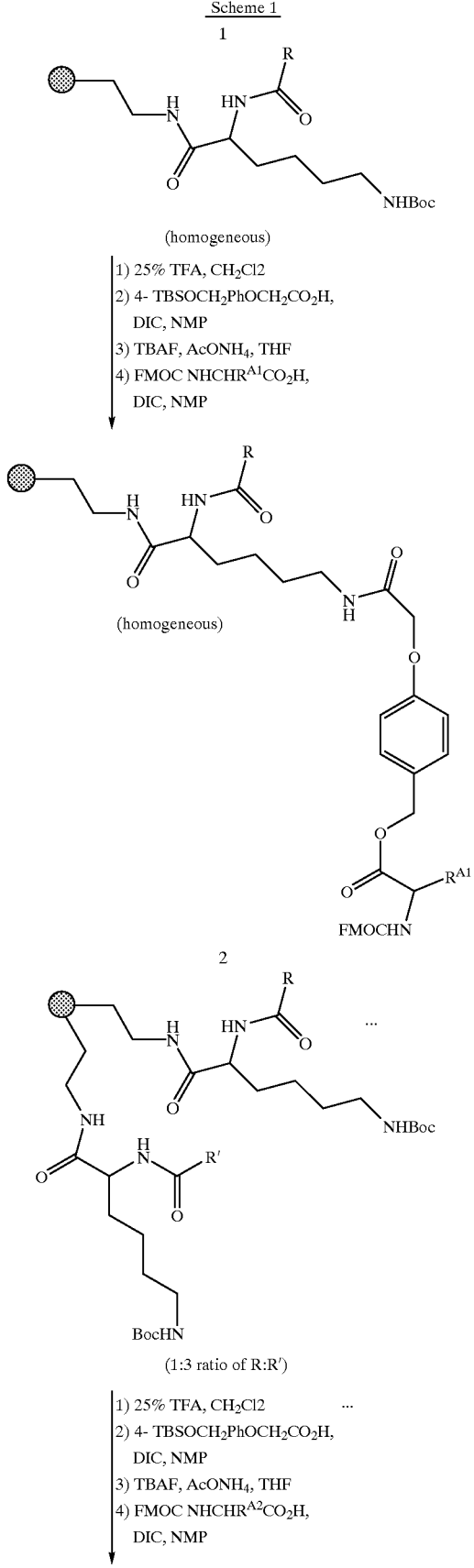
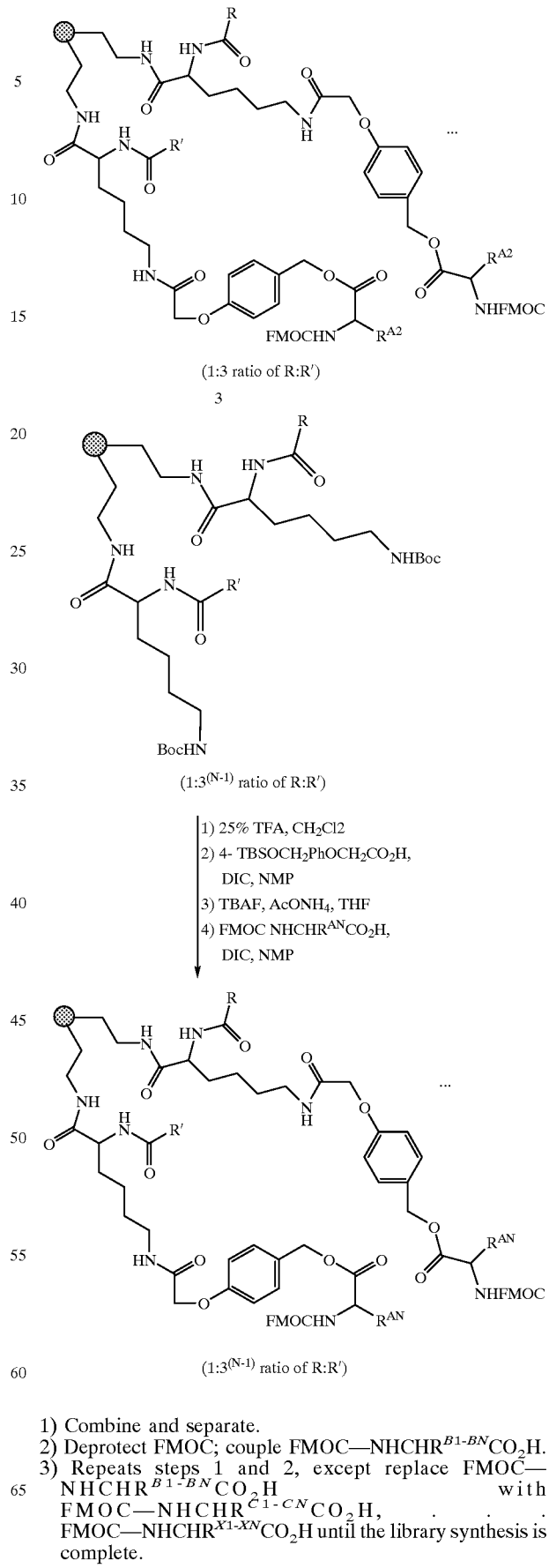
1) Combine and separate.
2) Deprotect FMOC; couple FMOC—NHCHR$^{B1-BN}$CO$_2$H.
3) Repeats steps 1 and 2, except replace FMOC—NHCHR$^{B1-BN}$CO$_2$H with FMOC—NHCHR$^{C1-CN}$CO$_2$H, . . . FMOC—NHCHR$^{X1-XN}$CO$_2$H until the library synthesis is complete.

4) Sort beads by flow cytometry.

5a) Cleave compounds off of sorted beads or

5b) Test compounds directly attached to beads, preferably by bio-panning or flow cytometry.

Scheme 1 outlines the preparation of a combinatorial library in which only the first registry has been encoded. As used in Scheme 1 beads with attached fluorescently labeled identifiers are derivatized with a linker that allows for cleavage of the compound to be tested. Subsequently, each group of similarly tagged beads is entered into a separate container and subjected to specified reaction conditions (or variable building blocks, as used herein) to form the first registry. Once the reaction is complete the beads are combined into a single mixture and then separated according to the number of choices in the second registry and reacted. This procedure of dividing beads, followed by subjection to specified reaction conditions, and then recombining beads is iterated until the first library is completed. The completed library is then tested for biological activity. Information on the relative activities of mixtures of the compounds with a homogeneous first registry is obtained from this library.

In carrying out the synthesis to prepare the second library, one will preferably begin with the same number of beads as used in the first library, said beads may be tagged in a similar manner as in the first library. The beads for use in the second library are first combined into a single mixture and then separated according to the number of choices for the first registry. The synthetic scheme\choices for each registry of the second library and all subsequent libraries will be substantially the same as the synthetic scheme\choices of the corresponding registry in the first library. Once the reaction (s) for the first registry of the second library is complete, one may wish to wash the beads free of any reagent, followed by combining all of the beads into a single mixture and then sorting the mixture into groups according to similarly tagged beads. Preferably this combination of beads will be sorted using flow cytometry. Once the beads from the first registry are sorted each group of similarly tagged beads is entered into a separate container and subjected to the same synthetic scheme(s)\choice(s) used for the second registry of the first library. Once the reaction(s) is complete, one may wish to wash the beads free of any reagent, followed by combining all of the beads into a single mixture and then separating the beads according to the number choices in the third registry of the first library. This procedure of dividing beads, followed by the synthetic scheme(s)\choice(s) from the corresponding registry of the first library, and then recombining the beads is iterated until the second library in completed.

The library thus prepared will contain tagged beads which identify the reaction sequence of the second registry only.

A combinatorial library containing tagged beads which identify the reaction sequence of the second registry only can be prepared as outlined in Scheme 2 below.

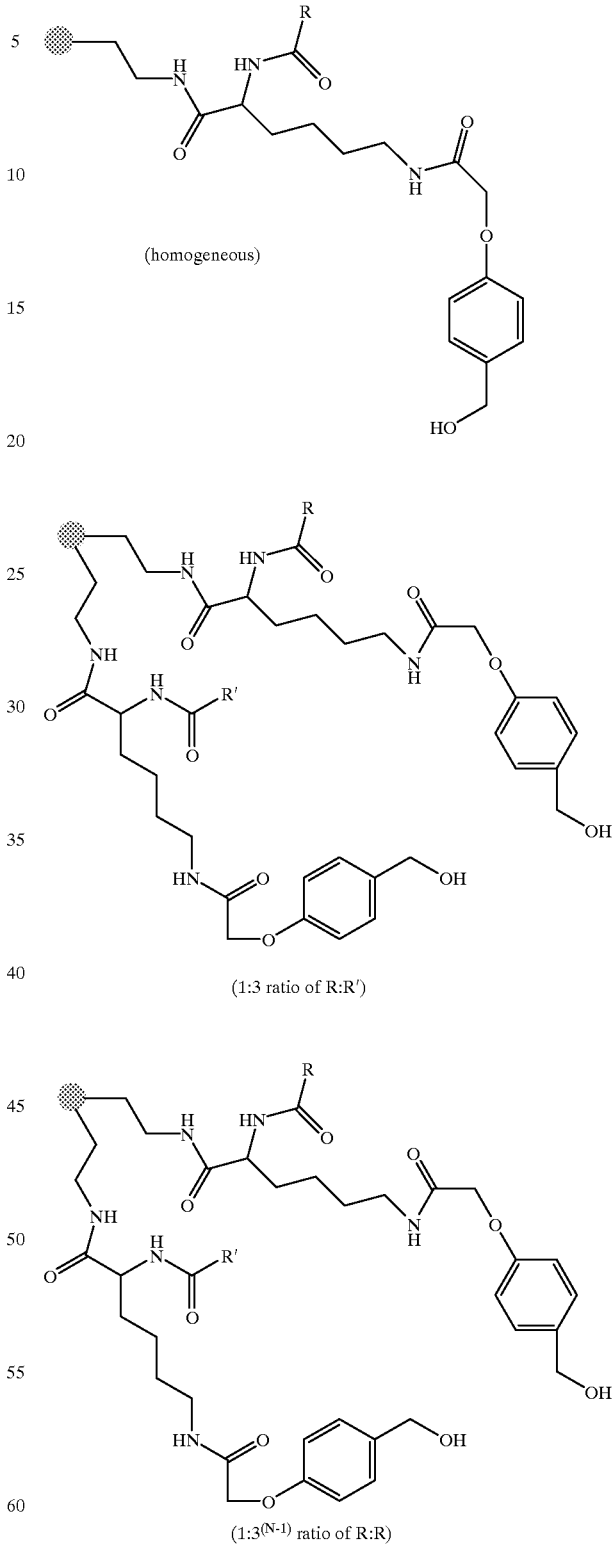

Scheme 2

(homogeneous)

(1:3 ratio of R:R′)

(1:3$^{(N-1)}$ ratio of R:R)

(as prepared in Schemes 1 and 3)
1) Combine and separate.
2) Couple FMOC—NHCHR$^{A1-AN}$CO$_2$H
3) Combine and sort by flow cytometry. .

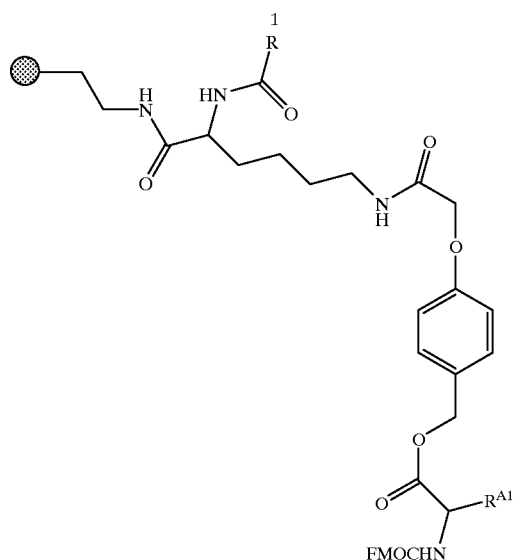
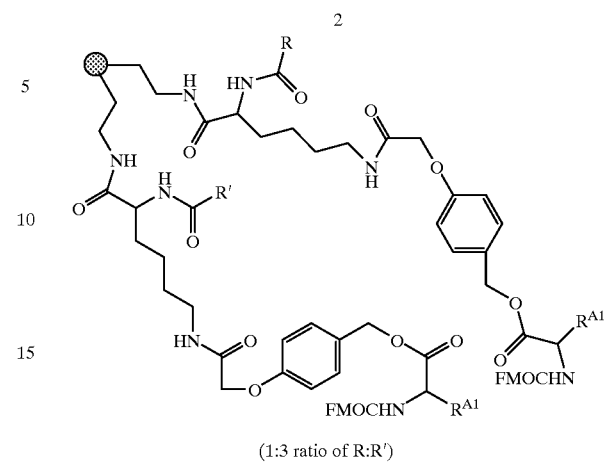
(1:3 ratio of R:R')
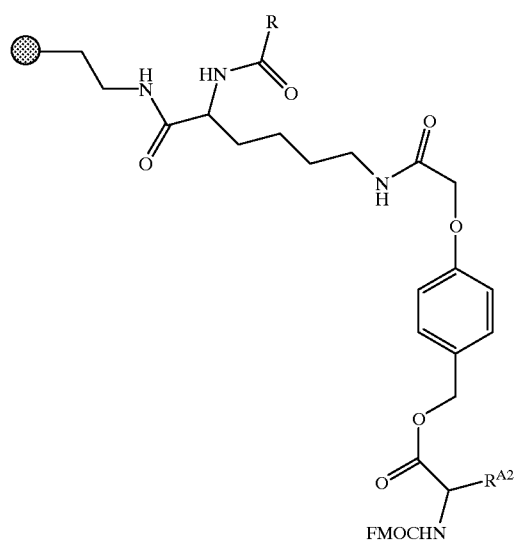
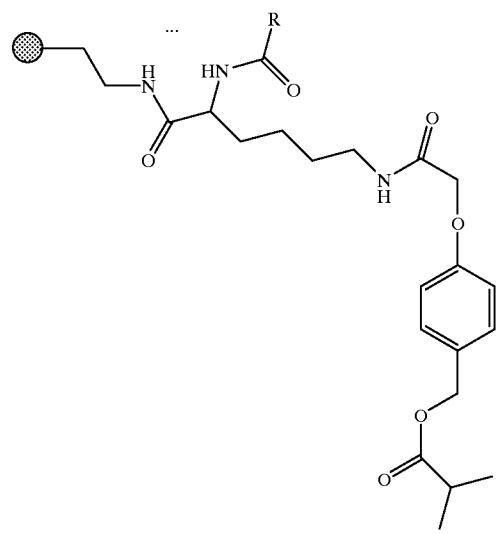
(1:3 ratio of R:R')
(1:3 ratio of R:R')

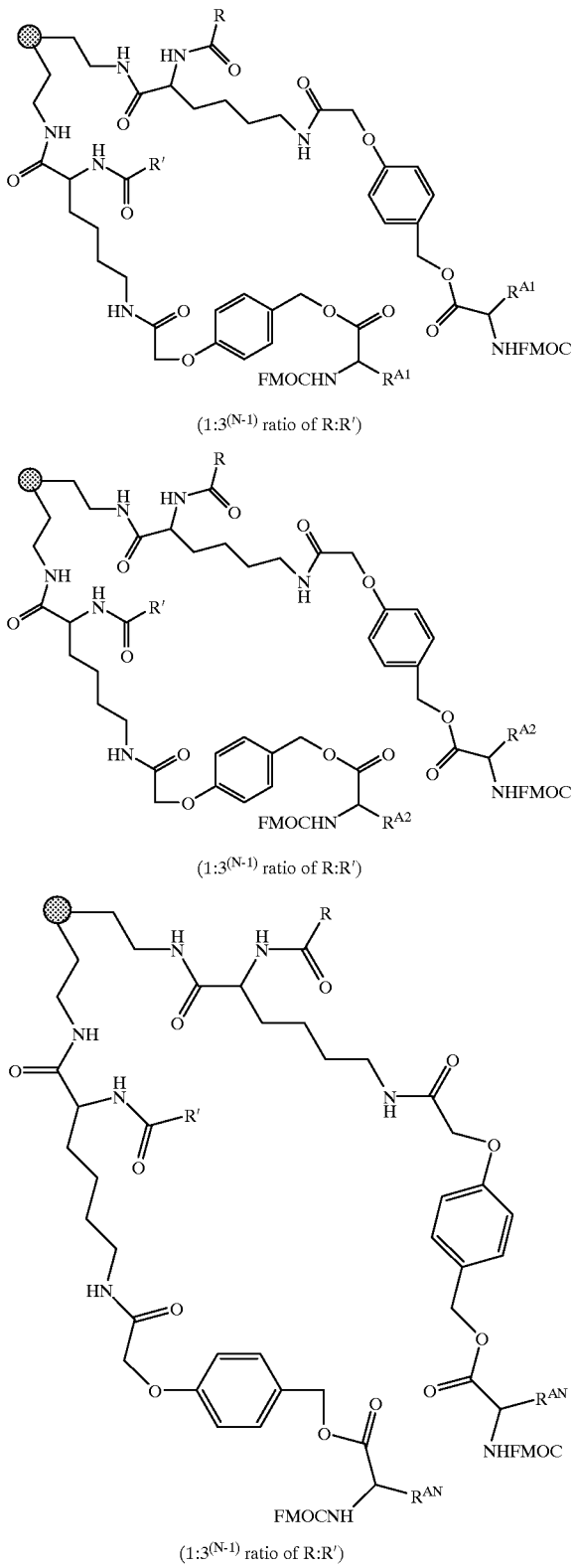

(1:3^(N-1) ratio of R:R′)

(1:3^(N-1) ratio of R:R′)

(1:3^(N-1) ratio of R:R′)

4) Deprotect FMOC; couple FMOC—NHCHR$^{B1-BN}$CO$_2$H.
5) Combine and separate.
6) Repeat step 4 and 5, except replace FMOC—NHCHR$^{B1-BN}$CO$_2$H with FMOC—NHCHR$^{C1-CN}$CO$_2$H, . . . FMOC—NHCHR$^{X1-XN}$CO$_2$H until the synthesis is complete.
7) Combine and sort by flow cytometry.
8a) Cleave compounds off of sorted beads or
8b) Test compounds directly attached to beads, preferably by bio-panning or flow cytometry.

Scheme 2 outlines the preparation of a combinatorial library in which only the second registry has been encoded. As used in Scheme 2 beads with attached fluorescent label identifiers are first combined into a single mixture and then separated into groups according to the number of choices in the first registry of the first library. Subsequently, each group is entered into a separate container and subjected to the same reaction conditions of the first registry of the first library to form the first registry of the second library. Once the reaction(s) is complete the beads are combined into a single mixture and then sorted into groups according to similarly tagged beads. Preferably this combination of beads will be sorted using flow cytometry. Each group of similarly tagged beads is entered into a separate container and subjected to the same reaction conditions of the second registry of the first library to form the second registry of the second library. Once the reaction is complete the beads are combined into a single mixture and then separated according to the number of choices in the third registry of the first library and reacted accordingly. This procedure of dividing the beads, followed by subjection to specified reaction conditions from the corresponding registry of the first library, and then recombining the beads is iterated until the second library is completed. The completed library is then tested for biological activity. Information on the relative activities of mixtures of the compounds with a homogeneous second registry is obtained from this library.

The above process is repeated to prepare subsequent libraries (when desired), provided that the sorting procedure is performed prior to a different synthetic stage in each library. The combinatorial libraries thus prepared will contain tagged beads which identify the reaction sequence of a single registry only. Further, the identifiable\encoded registry in each combinatorial library will be different.

Subsequent Combinatorial Libraries

The preparation of a combinatorial library in which the Xth registry has been encoded utilizes the same procedure as described in Scheme 2 except that the "combine and sort, preferably by flow cytometry" step is performed just prior to incorporation of the Xth variable building block. The completed library is then tested for biological activity. Information on the relative activities of mixtures of the compounds with a homogeneous Xth variable registry is obtained from this library.

After synthesis is complete, each library is tested separately for biological activity.

The term "testing for biological activity" or "testing for desired characteristics" as used herein includes any form of testing for pharmaceutical activity including the methods indicated below. The compounds of a library may be tested on the beads, for example by bio-panning using a soluble receptor assay, and the activities analyzed preferably by flow cytometry. Alternatively, the contents of the library may be sorted preferably by flow cytometry and the compounds tested on the beads, or the sorted compounds cleaved from the beads prior to testing.

When all of the information is combined, a population analysis of each combinatorial library is obtained revealing which variable building block(s) are important for activity and which ones are not. This type of analysis is identical to Structure Activity Relationship (SAR) studies in which the analysis of actives and inactives identify essential moieties in a lead structure. In this analysis a particular lead structure may be obtained, further multiple lead structures are potentially obtained (as in positional scanning in peptide combinatorial libraries) and initial directions for further optimization are immediately suggested.

The analysis of a three (3) registry-three (3) combinatorial library, prepared as in the above Schemes, is outlined in Table 1 below.

TABLE 1

First combinatorial library with encoded first Registry prepared as in Scheme 1 above.

|       | Registry 1 |   | Registry 2 |   | Registry 3 |
|-------|------------|---|------------|---|------------|
| $T^1$ | $A^1$      | — | X          | — | X          |
| $T^2$ | $A^2$      | — | X          | — | X          |
| $T^3$ | $A^3$      | — | X          | — | X          |

Second combinatorial library with encoded second Registry prepared as in Scheme 2 above.

|       | Registry 1 |      | Registry 2 |   | Registry 3 |
|-------|------------|------|------------|---|------------|
| $T^1$ | X          | Sort → | $B^1$      | — | X          |
| $T^2$ | X          | →    | $B^2$      | — | X          |
| $T^3$ | X          | →    | $B^3$      | — | X          |

Third combinatorial library with encoded third Registry prepared as indicated in 'Subsequent Combinatorial Libraries' above.

|       | Registry 1 |   | Registry 2 |      | Registry 3 |
|-------|------------|---|------------|------|------------|
| $T^1$ | X          | — | X          | Sort → | $C^1$      |
| $T^2$ | X          | — | X          | →    | $C^2$      |
| $T^3$ | X          | — | X          | →    | $C^3$      |

Analysis of the first combinatorial library will yield the SAR of variable building block A. Analysis of the second combinatorial library will yield the SAR of variable building block B. Analysis of the third combinatorial library will yield the SAR of variable building block C. Analysis of the SARs of the three variable building blocks (A, B and C) will identify desired reaction sequences and suggest multiple lead structures.

In a further aspect of the invention there is provided a preferred method for encoding\tagging combinatorial libraries which utilizes fluorescent label identifiers. As used herein, the term "fluorescent label identifiers" when referring to fluorophore labeled beads means:

i) that all of the beads in a given pool will have the same fluorescence intensity and different pools will have intensities that differ from any other pool by a factor of at least 2, preferably 3 or more or ii) that multiple, preferably 2, different fluorescent tags are used in varying ratios such that all of the beads in a given pool will have the same combination of fluorescent tags in the same ratio and different pools will have:

a) the same fluorescent tags but in ratios that differ from any other pool, b) a different set of fluorescent tags in a specified ratio or c) a combination of a) and b).

It is known that flow cytometers are able to sort beads that differ in fluorescence intensity by a factor of 2. The principles of flow cytometry and general methods for using flow cytometry are described in Grogan and Collins, *Guide to Flow Cytometry Methods*, Pub: Marcel Dekker, Inc. (1990).

Intensity-differentiated fluorophore-labeled beads can be prepared by derivatizing pools of beads with varying amounts of a fluorophore and a non-fluorophore or by varying the reaction time of a single reactive fluorescent tag. Additionally, multiple, preferably 2, fluorescent tags can be used in varying ratios to encoded beads. This is preferably implemented, for example, by varying the stoichiometry of a first fluorescent tag (A) and a second fluorescent tag (B), such as A:B=1:1, 1:2, 2:1, 1:4, 4:1, etc., in the tagging step(s).

As used herein, intensity-differentiated fluorophore-labeled beads can be prepared by the method outlined in Scheme 3 below and in the Examples.

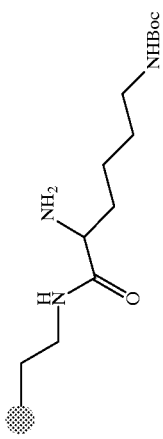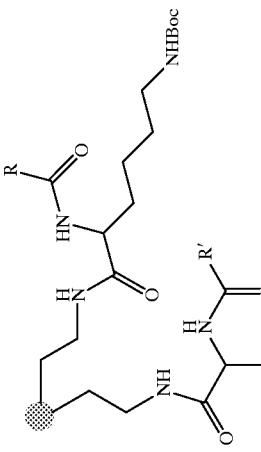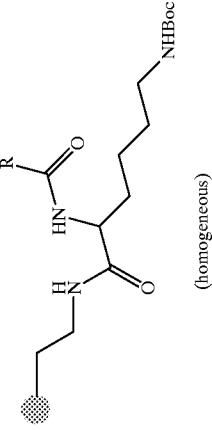

As used in Schemes 1 to 3 above, R is a fluorescent tag $T^1$ or a doping agent D and R' is a fluorescent tag$T^2$ or a doping agent D, provided that when R is D, R' is other than D.

As used in Scheme 3 a sample of beads, preferably Tentagel, 10–30 micron particles, is derivatized with a linker, preferably ε-Boc-FMOC lysine, by standard coupling chemistry. Alternatively, a benzyl alcohol linker such as used with the Wang linker or a benzyl halide linker such as used with the Merrifield linker, or a benzhydryl amine linker as used with the Rink linker can be attached to the beads by the formation of ethers by alkylation of alcohols, alkylation or arylation by Friedl Crafts chemistry, the formation of biaryls by palladium mediated cross-coupling chemistry or by standard amide coupling chemistry. As used in Scheme 3, a mono-deprotection step, such as 20% piperdine/DMF, for removal of an FMOC is performed. One could also run the tagging reaction to partial completion by limiting the reaction times thereby avoiding the use of a bifunctional linker. The beads are then divided into N pools. Pool 1 is derivatized with a fluorophore, such as pyrene butyric acid. Pool 2 is derivatized with a 1:3 mixture of a fluorophore, such as pyrene butyric acid, and a non-fluorophore (hereinafter a "doping agent"), such as butyric acid or a different fluorophore, such as perylene butyric acid. Pool N is derivatized with a $1:3^{(N-1)}$ ratio of a fluorophore, such as pyrene butyric acid, and a doping agent, such as butyric acid or a different fluorophore, such as perylene butyric acid.

Each of these pools of beads can be differentiated from any other pool of beads by flow cytometry. Each pool of beads may also be differentiated from one another by inspection with the unaided eye, however fewer variables could be encoded this way. Further, different fluorophores with different absorption and emittance wavelengths and multiple fluorophores could be encoded by fluorescence quenching to encode additional variables. The use of multiple fluorophores, the ratio of which is the identifier, has several advantages including the ability to greatly increases the number of variables that can be identified by using the same number of tags and enabling analysis independent of bead size. Also, the same strategy can be applied to prepare beads that can be used to discriminate between library members with redundant molecular weights by fluorescence, preferably by starting with beads with at least 50 pmoles of linker.

In a particularly preferred aspect of the invention a single combinatorial library is prepared, each choice therein being encoded by a tag, preferably using fluorescent label identifiers, and tested for biological activity, preferably without mixing the final pools.

In an especially preferred aspect of the invention the "Combine and Split protocol", as described in Scheme 4 below, is utilized to synthesize encoded beads, preferably with fluorescent label identifiers attached thereto. The "Combine and Split protocol" is advantageous in that it eliminates the need to resynthesize, or parallel synthesize, libraries containing only one or two fluorescent tags. This aspect of the invention is especially attractive from a practical point of view since the encoded beads can be prepared in bulk, prior to the actual synthesis of combinatorial libraries.

An additionally preferred aspect of this invention relates to combinatorial libraries prepared using beads encoded by fluorescent label identifiers and to pharmaceutically active compounds identified by such combinatorial library.

An additionally preferred aspect of this invention relates to combinatorial libraries in which each choice therein is encoded by fluorescent label identifiers and to pharmaceutically active compounds identified by such combinatorial library.

An additionally preferred aspect of this invention relates to combinatorial libraries prepared using beads encoded by fluorescent label identifiers, wherein said beads were obtained by the Combine and Split protocol, and to pharmaceutically active compounds identified by such combinatorial library.

An additionally preferred aspect of this invention relates to combinatorial libraries in which each choice therein is encoded by fluorescent label identifiers, wherein said beads were obtained by the Combine and Split protocol, and to pharmaceutically active compounds identified by such combinatorial library.

An example of a combinatorial library prepared according to the present invention is outlined in Scheme 4 below.

Scheme 4
Pool of Untagged Beads

OOOOOOO
STEP 1

Add permutations (1, 2 and 3 as used in Scheme 4) of identifier T(a) (either by adding varying ratios of a fluorophore and a non-fluorophore or by adding two different fluorescent tags in varying ratios)

↓ $T_{1a}$     ↓ $T_{2a}$     ↓ $T_{3a}$

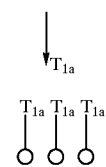    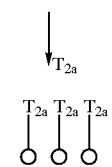    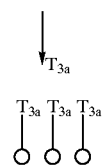

Combine and Split

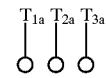    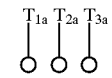    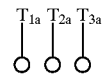

-continued

STEP 2
Add permutations (1, 2 and 3 as used in Scheme 4) of identifier T(b) (either by adding varying ratios of a fluorophore and a non-fluorophore or by adding two different fluorescent tags in varying ratios)

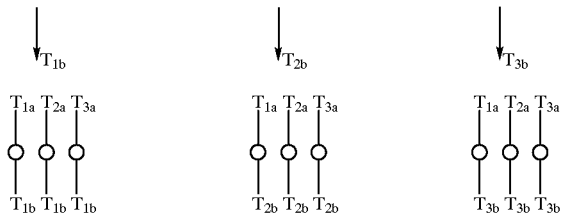

Combine and Split

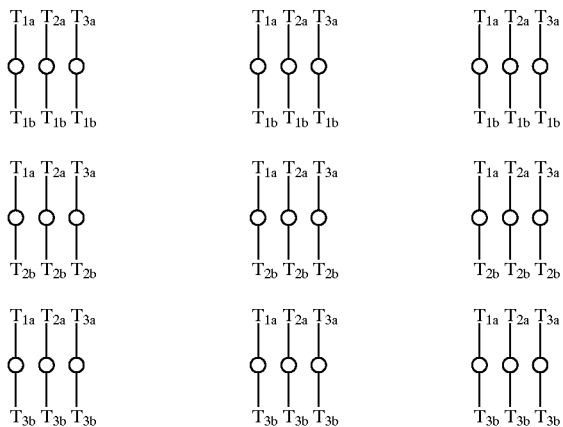

STEP 3
Add permutations (1, 2 and 3 as used in Scheme 4) of identifier T(c) (either by adding varying ratios of a fluorophore and a non-fluorophore or by adding two different fluorescent tags in varying ratios)

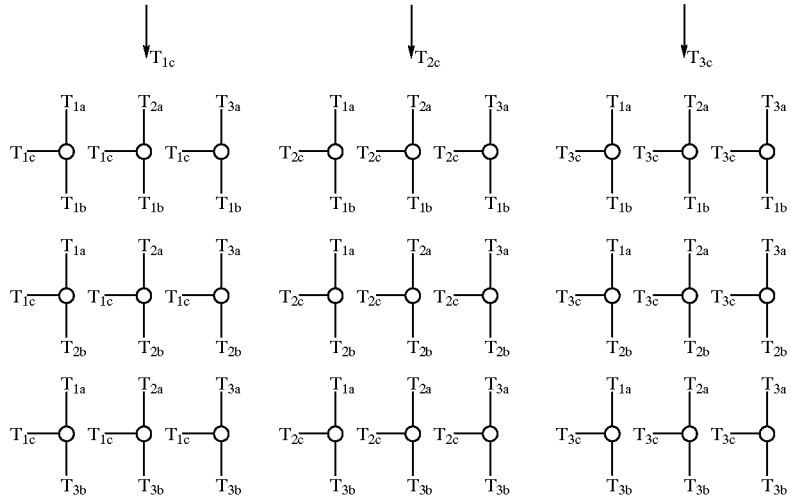

STEP 4
Conduct Specified Reaction Conditions

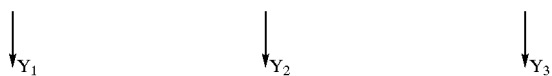

-continued

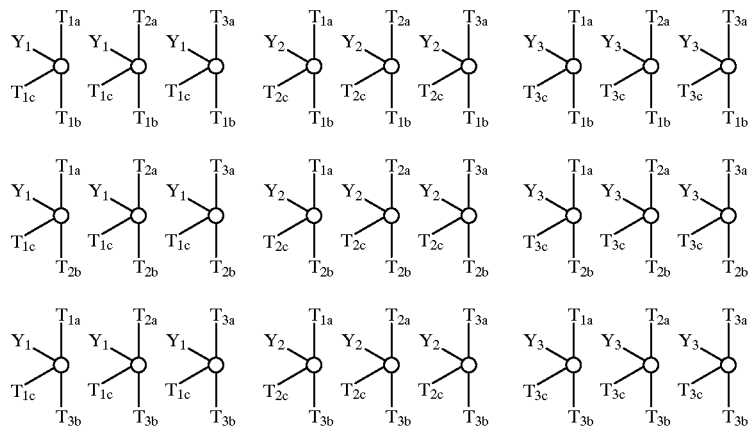

as such:
$Y_1$ is encoded by $T_{1c}$
$Y_2$ is encoded by $T_{2c}$
$Y_3$ is encoded by $T_{3c}$ STEP 5
Combine and Sort by $T_{xa}$. As used throught Scheme 4, x is 1, 2 or 3 as utilized above

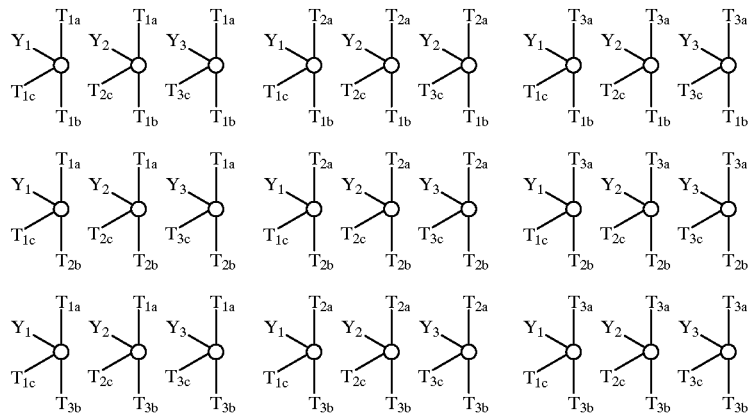

The above $T_{1a}$ Registry can be described as $$T_{1a} \begin{bmatrix} Y_x \\ T_{xb} \\ T_{xc} \end{bmatrix}$$

using the abbreviated terminology

The above $T_{2a}$ Registry can be described as $$T_{2a} \begin{bmatrix} Y_x \\ T_{xb} \\ T_{xc} \end{bmatrix}$$

using the abbreviated terminology

The above $T_{3a}$ Registry can be described as $$T_{3a} \begin{bmatrix} Y_x \\ T_{xb} \\ T_{xc} \end{bmatrix}$$

using the abbreviated terminology

Conduct specified reaction conditioins $\downarrow Z_1$ $\downarrow Z_2$ $\downarrow Z_3$ $$T_{1a} \begin{bmatrix} Y_{\bar{x}}{-}Z_1 \\ T_{xb} \\ T_{xc} \end{bmatrix} \quad T_{2a} \begin{bmatrix} Y_{\bar{x}}{-}Z_2 \\ T_{xb} \\ T_{xc} \end{bmatrix} \quad T_{3a} \begin{bmatrix} Y_{\bar{x}}{-}Z_3 \\ T_{xb} \\ T_{xc} \end{bmatrix}$$

Using the above abbreviated terminology as such:
$Z_1$ is encoded by $T_{1a}$
$Z_2$ is encoded by $T_{2a}$
$Z_3$ is encoded by $T_{3a}$ -continued STEP 6
Combine and sort by $T_{xb}$.

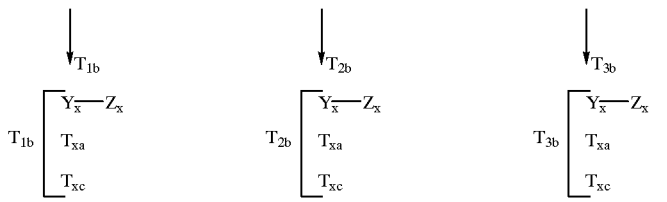

Conduct specified reaction conditions

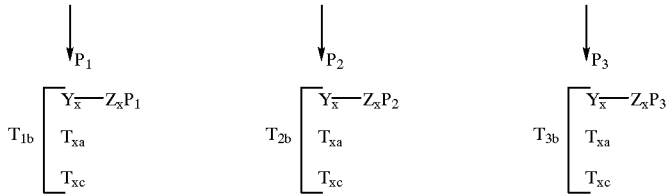

as such:
    $P_1$ is encoded by $T_{1h}$    $P_2$ is encoded by $T_{2h}$    $P_3$ is encoded by $T_{3h}$ STEP 7
Combine and Split

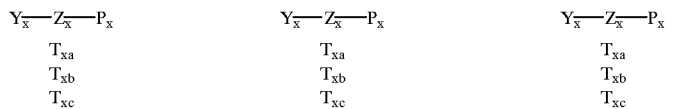

Conduct Specified Reaction Conditions

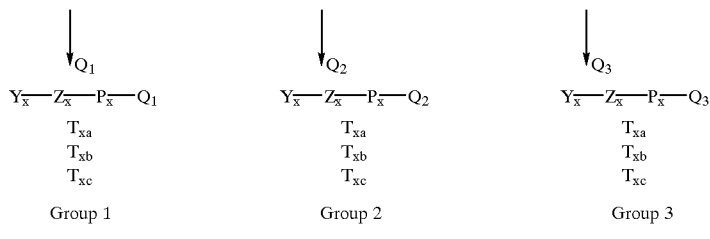

Group 1        Group 2        Group 3

Scheme 4 outlines the preparation of a combinatorial library in which each choice therein is encoded by a unique identifier. As used in Scheme 4 untagged beads are encoded with the first identifier (as described in Scheme 3). The encoded beads are combined into a single mixture and then separated into groups according to the number of permutations of the second identifier. The beads are then encoded with the second identifier. (The above encoding process is repeated until groups of encoded beads of desired size is obtained). According to Scheme 4, the beads encoded with the second identifier are combined into a single mixture and then separated into groups according to the number of permutations of the third identifier. The beads are then encoded with the third identifier.

Encoded beads prepared according to the above methods and said methods represent preferred embodiments of the claimed invention.

The beads thus prepared are maintained in separate homogeneous pools of like identifiers according to the third identifier and subjected to the first stage (or registry as used herein) of specified reaction conditions. The choices of the first registry are thereinby encoded by the third identifier. The beads are then combined and sorted, preferably by flow cytometry, into homogeneous pools of like identifiers according to the first identifier. The beads thus obtained are maintained in separate pools and subjected to the second stage of specified reaction conditions. The choices of the second registry are thereinby encoded by the first identifier. The beads are then combined and sorted, preferably by flow cytometry, into homogeneous pools of like identifiers according to the second identifier. The beads thus obtained are maintained in separate pools and subjected to the third stage of specified reaction conditions. The choices of the third registry are thereinby encoded by the second identifier. The beads are then combined and separated into groups according to the number of choices of the forth stage and subjected to the forth stage of specified reaction conditions. The pools of beads thus obtained are maintained in these separate groups and tested for biological activity. The choices of the forth registry are thereinby separately maintained.

As indicated above, each of these groups are separately tested for biological activity and analyzed, preferably by flow cytometry or by cleavage of compounds from individual groups or from smaller sets of individual groups. The exact reaction history of each active can be identified by reading the unique identifier from the corresponding bead. In the above Scheme, if an active compound is found in group 2 then one could analyze the individual bead by fluorescence detection. If $T_{3c}$, $T_{2a}$, $T_{2b}$ were present on the bead, then the reaction history of the active structure is: $Y_3$—$Z_2$—$P_2$—$Q_2$.

By the term "Combine and Split protocol" as used herein is analogously described by the steps of Scheme 4 above. The formation of encoded beads by the Combine and Split protocol is analogously described in steps 1 to 4 of Scheme 4. The formation of combinatorial library in which each choice therein is encoded by the Combine and Split protocol is analogously described in steps 1 to 7 of Scheme 4.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1

Preparation of fluorophore-labeled beads that can be sorted by flow cytometry by differences in the intensity of fluorescence by the method of doping.

Procedure A

A bifunctional linker such as e-Boc-FMOC-L-lysine (8.4 g, 6 eq., 18 mmol, Novabiochem), an amide coupling agent such as diisopropyl carbodiimide (2.3 g, 2.8 ml, 6 eq., 18 mmol, Aldrich) is added to Polyethylene glycol-linked to cross-linked polystyrene beads (Tentagel M $NH_2$, 10 micron particle size, 15.0 g, 3 mmol, Rapp Polymere) suspended in a suitable solvent such as N-methyl pyrrolidine (300 ml) and is agitated overnight The reaction is filtered through a glass frit under aspirator pressure and is washed with DMF (5×100 ml).

The beads are then agitated with 25% piperidine/DMF (300 ml) for 15 min. The reaction is filtered through a glass frit under aspirator pressure, washed with DMF (5×100 ml), then $CH_2Cl_2$ (5×100 ml), then air dried.

Procedure B

The lysine derivatized beads (5.0 g), as described in Procedure A, are suspended in N-methyl pyrrolidine (100 ml), then a fluorophore such as 1-pyrene butyric acid (1.7 g, 6 eq., 6 mmol, Aldrich) and diisopropyl carbodiimide (0.76 g, 0.94 ml, 6 mmol) are added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

The beads are then agitated in 25% TFA/$CH_2Cl_2$ (100 ml) for 2 h removing the Boc protective group. The reaction is filtered through a glass frit under aspirator pressure, washed with DMF (5×30 ml), then $CH_2Cl_2$ (5×30 ml), then air dried.

The beads are then reacted with a linker group such as the t-butyl dimethyl silyl ether of 4(methyl hydroxy-phenyl) acetic acid (1.3 g, 6 mmol), diisopropyl carbodiimide (0.76 g, 0.94 ml, 6 mmol) in N-methyl pyrrolidine (100 ml) overnight. The reaction is filtered through a glass frit under aspirator pressure and is washed with DMF (5×30 ml), then $CH_2Cl_2$ (5×100 ml), then air dried.

The beads are then re suspended in THF (100 ml), and a desilylating agent such as tetrabutyl ammonium fluoride(6 ml, 1.0 M solution, 6 mmol, Aldrich)/ammonium acetate (0.92 g, 12 mmol) is used to deprotect the silyl ether producing the desired benzyl alcohol derivative. The reaction is filtered through a glass frit under aspirator pressure, washed with DMF (5×30 ml), then $CH_2Cl_2$ (5×30 ml), then air dried.

Procedure C

The beads (5 g), as prepared in Procedure B, are then suspended in N-methyl pyrrolidine (100 ml) and is then reacted with a monomer such as FMOC-L-glyine (1.8 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then CH2Cl2 (5×30 ml), then air dried. This procedure is repeated until the reaction is complete by the Kaiser ninhydrin test.

Procedure D

The lysine derivatized beads (5.0 g), as described in Procedure A, are suspended in N-methyl pyrrolidine (100 ml), then a fluorophore such as 1-pyrene butyric acid (0.43 g, 1.5 eq., 1.5 mmol), and a doping agent such as butyric acid (0.4 g, 0.41 ml, 4.5 eq., 4.5 mmol) in 1:3 stoichiometry, and diisopropyl carbodiimide (0.76 g, 0.94 ml, 6 mmol) are added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

The beads are then agitated in 25% TFA/$CH_2Cl_2$ (100 ml) for 2 h removing the Boc protective group. The reaction is filtered through a glass frit under aspirator pressure, washed with DMF (5×30 ml), then $CH_2Cl_2$ (5×30 ml), then air dried.

The beads are then reacted with a linker group such as the t-butyl dimethyl silyl ether of 4-(methyl hydroxy-phenyl) acetic acid (1.3 g, 6 mmol), diisopropyl carbodiimide (0.76 g, 0.94 ml, 6 mmol) in N-methyl pyrrolidine (100 ml) overnight. The reaction is filtered through a glass frit under aspirator pressure and is washed with DMF (5×30 ml), then $CH_2Cl_2$ (5×100 ml), then air dried.

The beads are then resuspended in THF (100 ml), and a desilylating agent such as tetrabutyl ammonium fluoride(6 ml, 1.0 M solution, 6 mmol, Aldrich)/ammonium acetate (0.92 g, 12 mmol) is used to deprotect the silyl ether producing the desired benzyl alcohol derivative. The reaction is filtered through a glass frit under aspirator pressure, washed with DMF (5×30 ml), then $CH_2Cl_2$ (5×30 ml), then air dried.

Procedure E

The beads (5 g), as prepared in Procedure D, are then suspended in N-methyl pyrrolidine (100 ml) and is then reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure F

The lysine derivatized beads (5.0 g), as described in Procedure A, are suspended in N-methyl pyrrolidine (100 ml), then a fluorophore such as 1-pyrene butyric acid (0.173 g, 0.6 eq., 0.6 mmol), and a doping agent such as butyric acid (0.48 g, 0.49 ml, 5.4 eq., 5.4 mmol) in 1:9 stoichiometry, and diisopropyl carbodiimide (0.76 g, 0.94 ml, 6 mmol) are added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

The beads are then agitated in 25% TFA/$CH_2Cl_2$ (100 ml) for 2 h removing the Boc protective group. The reaction is filtered through a glass frit under aspirator pressure, washed with DMF (5×30 ml), then $CH_2Cl_2$ (5×30 ml), then air dried.

The beads are then reacted with a linker group such as the t-butyl dimethyl silyl ether of 4-(methyl hydroxy-phenyl) acetic acid (1.3 g, 6 mmol), diisopropyl carbodiimide (0.76 g, 0.94 ml, 6 mmol) in N-methyl pyrrolidine (100 ml) overnight. The reaction is filtered through a glass frit under aspirator pressure and is washed with DMF (5×30 ml), then $CH_2Cl_2$ (5×100 ml), then air dried.

The beads are then resuspended in ThF (100 ml), and a desilylating agent such as tetrabutyl ammonium fluoride(6 ml, 1.0 M solution, 6 mmol, Aldrich)/ammonium acetate (0.92 g, 12 mmol) is used to deprotect the silyl ether producing the desired benzyl alcohol derivative. The reaction is filtered through a glass frit under aspirator pressure, washed with DMF (5×30 ml), then $CH_2Cl_2$ (5×30 ml), then air dried.

Procedure G

The beads (5 g), as prepared in Procedure F, are then suspended in N-methyl pyrrolidine (100 ml) and is then reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure H

The beads obtained from procedures C, E, and G are then combined and split into 3 equal portions.

Pool H1 is reacted with a monomer such as FMOC-L-glyine (1.8 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool H2 is reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool H3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure I

The beads obtained from Procedure H are then combined and split into 3 equal portions.

Pool I1 is reacted with a monomer such as FMOC-L-glyine (1.8 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried This procedure is repeated until the reaction is complete by the Kaiser ninhydrin test.

Pool I2 is reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool I3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure J

The beads obtained from Procedure I are then combined and sorted by flow cytometry into different sublibraries differentiated by the differences in intensity of fluorescence. Sublibrary components have the same first amino acid of the tripeptide.

Sublibrary J1 consists of Gly-X-X or Gly-Gly-Gly, Gly-Gly-Ala, Gly-Gly-Phe, Gly-Ala-Gly, Gly-Ala-Ala, Gly-Ala-Phe, Gly-Phe-Gly, Gly-Phe-Ala, Gly-Phe-Phe.

Sublibrary J2 consists of Ala-X-X or Ala-Gly-Gly, Ala-Gly-Ala, Ala-Gly-Phe, Ala-Ala-Gly, Ala-Ala-Ala, Ala-Ala-Phe, Ala-Phe-Gly, Ala-Phe-Ala; Ala-Phe-Phe Sublibrary J3 consists of Phe-X-X or Phe-Gly-Gly, Phe-Gly-Ala, Phe-Gly-Phe, Phe-Ala-Gly, Phe-Ala-Ala, Phe-Ala-Phe, Phe-Phe-Gly, Phe-Phe-Ala, Phe-Phe-Phe Procedure K The beads obtained from Procedure B, D, and F are then combined and split into 3 equal portions.

Pool K1 is reacted with a monomer such as FMOC-L-glyine (1.8 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool K2 is reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool K3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure L

The beads obtained from Procedure K are then combined and sorted by flow cytometry into different pools differentiated by the differences in intensity of fluorescence.

Pool L1 is reacted with a monomer such as FMOC-L-glyine (1.8 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool L2 is reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool L3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure M

The beads obtained from Procedure L are then combined and split into 3 equal portions.

Pool M1 is reacted with a monomer such as FMOC-L-glyine (1.8 g, $^6$ eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool M2 is reacted with a monomer such as FMOC-L-alanine (1.9 g, $^6$ eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool M3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure N

The beads obtained from Procedure M are then combined and sorted by flow cytometry into different sublibraries differentiated by the differences in intensity of fluorescence. Sublibrary components have the same second amino acid of the tripeptide.

Sublibrary N1 consists of X-Gly-X or Gly-GlyGly, Gly-Gly-Ala, Gly-Gly-Phe, Ala-Gly-Gly, Ala-Gly-Ala, Ala-Gly-Phe, Phe-Gly-Gly, Phe-Gly-Ala, Phe-Gly-Phe Sublibrary N2 consists of X-Ala-X or Gly-Ala-Gly, Gly-Ala-Ala, Gly-Ala-Phe, Ala-Ala-Gly, Ala-Ala-Ala, Ala-Ala-Phe, Phe-Ala-Gly, Phe-Ala-Ala, Phe-Ala-Phe Sublibrary N3 consists of X-Phe-X or Gly-Phe-Gly, Gly-Phe-Ala, Gly-Phe-Phe, Ala-Phe-Gly, Ala-Phe-Ala, Ala-Phe-Phe, Phe-Phe-Gly, Phe-Phe-Ala, Phe-Phe-Phe Procedure O The beads (5.0 g), as described in Procedure K, are combined and split into 3 equal portions.

Pool O1 is reacted with a monomer such as FMOC-L-glyine (1.8 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool O2 is reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered though a glass frit under aspirator pressure, washed with DMF (5×30 ml), then $CH_2Cl_2$ (5×30 ml), then air dried. This procedure is repeated until the reaction is complete by the Kaiser ninhydrin test.

Pool O3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure P

The beads obtained from Procedure O are then combined and split into 3 equal portions.

Pool P1 is reacted with a monomer such as FMOC-L-glyine (1.8 g, $^6$ eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool P2 is reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool P3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Procedure Q

The beads obtained from Procedure P are then combined and sorted by flow cytometry into different pools differentiated by the differences in intensity of fluorescence.

Pool Q1 is reacted with a monomer such as FMOC-L-glyine (1.8 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool Q2 is reacted with a monomer such as FMOC-L-alanine (1.9 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

Pool Q3 is reacted with a monomer such as FMOC-L-phenylalanine (2.3 g, 6 eq., 6 mmol). Diisopropyl carbodiimide (0.76 g, 0.94 ml, 6 mmol) is added, and the reaction is agitated for 3 hours. The reaction is filtered through a glass frit under aspirator pressure, washed with DMF (5×30 ml), then $CH_2Cl_2$ (5×30 ml), then air dried. This procedure is repeated until the reaction is complete by the Kaiser ninhydrin test.

The pools of beads obtained from Procedure Q are already sorted into sublibraries in which the third amino acid of each component is the same the same amino acid of the tripeptide.

Sublibrary Q1 consists of X-X-Gly or Gly-Gly-Gly, Gly-Ala-Gly, Gly-Phe-Gly, Ala-Gly-Gly, Ala-Ala-Gly, Ala-Phe-Gly, Phe-Gly-Gly, Phe-Ala-Gly, Phe-Phe-Gly Sublibrary Q2 consists of X-X-Ala or Gly-Gly-Ala, Gly-Ala-Ala, Gly-Phe-Ala, Ala-Gly-Ala, Ala-Ala-Ala, Ala-Phe-Ala, Phe-Gly-Ala, Phe-Ala-Ala, Phe-Phe-Ala Sublibrary Q3 consists of X-X-Phe or Gly-Gly-Phe, Gly-Ala-Phe, Gly-Phe-Phe, Ala-Gly-Phe, Ala-Ala-Phe, Ala-Phe-Phe, Phe-Gly-Phe, Phe-Ala-Phe, Phe-Phe-Phe Procedure R Individual sublibraries J1, J2, J3, N1, N2, N3, Q1, Q2, and Q3 are tested for biological activity either by cleaving the compounds from the beads with hydroxide or a strong acid such as HF or the compounds are tested on the beads by bio-panning or flow cytometry. The results from this testing gives a population analysis of preferred monomers in particular registries or positions.

EXAMPLE 2

Preparation of fluorophore-labeled beads that can be sorted by flow cytometry by differences in the intensity of fluorescence by the method of labeling with fluorophores whose emission maximum is at different wavelengths.

Procedure

The methods of Example 1 are used except that the doping reagent is replaced by a second fluorophore such as perylene butyric acid.

While the preferred embodiments of the invention are illustrated by the above, it is to be understood that the invention is not limited to the precise instructions herein disclosed and that the right to all modifications coming within the scope of the following claims is reserved.

What is claimed is:

1. A method of developing a structure activity relationship of essential moieties for a lead structure from a series of essentially the same combinatorial library prepared repeatedly from substantially the same specified set of reaction sequences to form a series of similar combinatorial libraries, which comprises:

a) preparing a first combinatorial library of the lead structure, wherein each reaction choice in the first registry is encoded, by
  i) sorting tagged beads into containers according to the number of reaction choices in the first registry, wherein the beads within each container are similarly tagged and each container contains uniquely tagged beads;
  ii) adding specified reagents under specified conditions to each container to complete the first registry;
  iii) combining all of the reacted beads into a single mixture and then separating the beads into containers according to the number of reaction choices in the next registry;
  iv) adding specified reagents under specified conditions to each container to complete the next registry;
  v) repeating steps iii) and iv) until the desired number of registries is obtained; and
  vi) optionally, combining the beads from the final registry into a single mixture;
b) preparing a second combinatorial library of the lead structure, wherein each choice in the second registry is encoded, by
  i) combining beads tagged similarly to those of a)–i) into a single mixture and then separating the beads into containers according to the number of reaction choices in the first registry;
  ii) adding specified reagents under specified conditions substantially according to the reaction choices in a)–ii) to each corresponding container to complete the first registry;
  iii) combining all of the reacted beads into a single mixture and then sorting the beads by flow cytometry into containers substantially according to the number of reaction choices in a)–iii), wherein the beads within each container are similarly tagged and each container contains uniquely tagged beads;
  iv) adding specified reagents under specified conditions to each container substantially according to the reaction choices in a)–iv) to each corresponding container to complete the second registry;
  v) repeating step a)–v) substantially according to the reaction choices of the corresponding registry in the first library until a number of registries corresponding to the first library is obtained; and
  vi) optionally, combining the beads from the final registry into a single mixture;
c) preparing subsequent libraries of the lead structure according the procedure in b) except that the sort step is performed prior to a different registry in each subsequent library, so that the number of libraries is substantially equal to the number of registries; and
d) developing a structure activity relationship based on a population analysis of each combinatorial library, by
  i) contacting the library components with a pharmaceutical target;
  ii) identifying beads containing active molecules by their encoded registry; and
  iii) determining the populations of active structures.

2. A method of developing a structure activity relationship of essential moieties for a lead structure from a series of essentially the same combinatorial library prepared repeatedly from substantially the same specified set of reaction sequences to form a series of similar combinatorial libraries, which comprises:

a) preparing a first combinatorial library of the lead structure, wherein each reaction choice in the first registry is encoded, by
  i) sorting beads into containers according to the number of reaction choices in the first registry, wherein the beads within one container are untagged and the beads within the other containers are tagged, and wherein the beads within each container are similarly tagged or untagged and each container of tagged beads contains uniquely tagged beads;
  ii) adding specified reagents under specified conditions to each container to complete the first registry;
  iii) combining all of the reacted beads into a single mixture and then separating the beads into containers according to the number of reaction choices in the next registry;
  iv) adding specified reagents under specified conditions to each container to complete the next registry;
  v) repeating steps iii) and iv) until the desired number of registries is obtained; and
  vi) optionally, combining the beads from the final registry into a single mixture;
b) preparing a second combinatorial library of the lead structure, wherein each choice in the second registry is encoded, by
  i) combining beads tagged similarly to those of a)–i) into a single mixture and then separating the beads into containers according to the number of reaction choices in the first registry;

ii) adding specified reagents under specified conditions substantially according to the reaction choices in a)–ii) to each corresponding container to complete the first registry;

iii) combining all of the reacted beads into a single mixture and then sorting the beads by flow cytometry into containers substantially according to the number of reaction choices in a)–iii), wherein the beads within each container are similarly tagged or untagged and each container of tagged beads contains uniquely tagged beads;

iv) adding specified reagents under specified conditions to each container substantially according to the reaction choices in a)–iv) to each corresponding container to complete the second registry;

v) repeating step a)–v) substantially according to the reaction choices of the corresponding registry in the first library until a number of registries corresponding to the first library is obtained; and vi) optionally, combining the beads from the final registry into a single mixture;

c) preparing subsequent libraries of the lead structure according the procedure in b) except that the sort step is performed prior to a different registry in each subsequent library, so that the number of libraries is substantially equal to the number of registries; and d) developing a structure activity relationship based on a population analysis of each combinatorial library, by i) contacting the library components with a pharmaceutical target;

ii) identifying beads containing active molecules by their encoded registry; and iii) determining the populations of active structures.

3. A method of encoding a series of combinatorial libraries of a lead structure wherein (i) each library is prepared by substantially the same reaction sequence, (ii) only one registry is encoded in each library and a different registry is encoded in each library, and (iii) each library is kept and analyzed separately, which comprises:

a) preparing a first combinatorial library of the lead structure, wherein each reaction choice in the first registry is encoded, by i) sorting tagged beads into containers according to the number of reaction choices in the first registry, wherein the beads within each container are similarly tagged and each container contains uniquely tagged beads;

ii) adding specified reagents under specified conditions to each container to complete the first registry;

iii) combining all of the reacted beads into a single mixture and then separating the beads into containers according to the number of reaction choices in the next registry;

iv) adding specified reagents under specified conditions to each container to complete the next registry;

v) repeating steps iii) and iv) until the desired number of registries is obtained; and vi) optionally, combining the beads from the final registry into a single mixture;

b) preparing a second combinatorial library of the lead structure, wherein each choice in the second registry is encoded, by i) combining beads tagged similarly to those of a)–i) into a single mixture and then separating the beads into containers according to the number of reaction choices in the first registry;

ii) adding specified reagents under specified conditions substantially according to the reaction choices in a)–ii) to each corresponding container to complete the first registry;

iii) combining all of the reacted beads into a single mixture and then sorting the beads by flow cytometry into containers substantially according to the number of reaction choices in a)–iii), wherein the beads within each container are similarly tagged and each container contains uniquely tagged beads;

iv) adding specified reagents under specified conditions to each container substantially according to the reaction choices in a)–iv) to each corresponding container to complete the second registry;

v) repeating step a)–v) substantially according to the reaction choices of the corresponding registry in the first library until a number of registries corresponding to the first library is obtained; and vi) optionally, combining the beads from the final registry into a single mixture; and c) preparing subsequent libraries of the lead structure according the procedure in b) except that the sort step is performed prior to a different registry in each subsequent library, so that the number of libraries is substantially equal to the number of registries; wherein the first, second and subsequent libraries are kept separate.

4. A method of encoding a series of combinatorial libraries of a lead structure wherein (i) each library is prepared by substantially the same reaction sequence, (ii) only one registry is encoded in each library and a different registry is encoded in each library, and (iii) each library is kept and analyzed separately, which comprises:

a) preparing a first combinatorial library of the lead structure, wherein each reaction choice in the first registry is encoded, by i) sorting beads into containers according to the number of reaction choices in the first registry, wherein the beads within one container are untagged and the beads within the other containers are tagged, and wherein the beads within each container are similarly tagged or untagged and each container of tagged beads contains uniquely tagged beads;

ii) adding specified reagents under specified conditions to each container to complete the first registry;

iii) combining all of the reacted beads into a single mixture and then separating the beads into containers according to the number of reaction choices in the next registry;

iv) adding specified reagents under specified conditions to each container to complete the next registry;

v) repeating steps iii) and iv) until the desired number of registries is obtained; and vi) optionally, combining the beads from the final registry into a single mixture;

b) preparing a second combinatorial library of the lead structure, wherein each choice in the second registry is encoded, by i) combining beads tagged similarly to those of a)–i) into a single mixture and then separating the beads into containers according to the number of reaction choices in the first registry;

ii) adding specified reagents under specified conditions substantially according to the reaction choices in a)–ii) to each corresponding container to complete the first registry;

iii) combining all of the reacted beads into a single mixture and then sorting the beads by flow cytometry into containers substantially according to the number of reaction choices in a)–iii), wherein the beads within each container are similarly tagged or untagged and each container of tagged beads contains uniquely tagged beads;

iv) adding specified reagents under specified conditions to each container substantially according to the reaction choices in a)–iv) to each corresponding container to complete the second registry;

v) repeating step a)–v) substantially according to the reaction choices of the corresponding registry in the first library until a number of registries corresponding to the first library is obtained; and vi) optionally, combining the beads from the final registry into a single mixture; and c) preparing subsequent libraries of the lead structure according the procedure in b) except that the sort step is performed prior to a different registry in each subsequent library, so that the number of libraries is substantially equal to the number of registries; wherein the first, second and subsequent libraries are kept separate.

* * * * *